United States Patent [19]
Kato et al.

[11] Patent Number: 5,763,763
[45] Date of Patent: Jun. 9, 1998

[54] METHOD AND SENSING DEVICE FOR MEASURING PREDETERMINED GAS COMPONENT IN MEASUREMENT GAS

[75] Inventors: Nobuhide Kato, Ama-gun; Noriyuki Ina, Okazaki; Yasushi Watanabe, Nagoya; Takao Murase, Konan, all of Japan

[73] Assignee: NGK Insulators, Ltd., Japan

[21] Appl. No.: 731,307

[22] Filed: Oct. 15, 1996

[30] Foreign Application Priority Data

Oct. 20, 1995 [JP] Japan ................. 7-272826

[51] Int. Cl.⁶ .................. G01N 27/46; G01N 27/58
[52] U.S. Cl. .................. 73/23.2; 73/23.32; 73/31.06; 204/412; 204/426; 204/429; 204/1 T
[58] Field of Search .................. 73/23.2, 23.32, 73/31.06; 204/412, 425, 426, 427, 428, 429, 1 T

[56] References Cited

U.S. PATENT DOCUMENTS

| | | | |
|---|---|---|---|
| 4,666,565 | 5/1987 | Dobson | 204/1 T |
| 4,668,374 | 5/1987 | Bhagat et al. | 204/412 |
| 4,728,411 | 3/1988 | Mase et al. | 204/425 |
| 4,755,274 | 7/1988 | Mase et al. | 204/427 |
| 4,770,760 | 9/1988 | Noda et al. | 204/425 |
| 4,795,544 | 1/1989 | Nishiazwa et al. | 204/425 |
| 4,882,033 | 11/1989 | Shibata et al. | 204/425 |
| 4,902,400 | 2/1990 | Usami et al. | 204/426 |
| 5,034,112 | 7/1991 | Murase et al. | 204/406 |
| 5,145,566 | 9/1992 | Logothetis et al. | 204/153.18 |
| 5,217,588 | 6/1993 | Wang et al. | 214/153.1 |
| 5,236,569 | 8/1993 | Murase et al. | 204/412 |
| 5,538,620 | 7/1996 | Nikolskaja | 205/782 |

FOREIGN PATENT DOCUMENTS

| | | |
|---|---|---|
| A 0257842 | 3/1988 | European Pat. Off. |
| 678 740 A1 | 10/1995 | European Pat. Off. |
| A 0 678 740 | 10/1995 | European Pat. Off. |
| A 0 731 351 | 9/1996 | European Pat. Off. |
| 4439901 A1 | 5/1996 | Germany |
| 64-39545 | 2/1989 | Japan |
| 1-277751 | 11/1989 | Japan |
| 2-1543 | 1/1990 | Japan |
| 6-72861 | 9/1994 | Japan |
| 8-29387 | 2/1996 | Japan |
| WO 95/30146 | 11/1995 | WIPO |

OTHER PUBLICATIONS

Patent Abstract or Japan, vol. 017, No. 231 (P-1532), 11 May 1993 & JP-A-04 359144 (Mitsubishi Motors Corp.), 11 Dec. 1992.

Primary Examiner—Hezron E. Williams
Assistant Examiner—J. David Wiggins
Attorney, Agent, or Firm—Parkhurst, Wendel & Burr, L.L.P.

[57] ABSTRACT

Disclosed is a method and a sensing device capable of measuring a predetermined measurement gas component continuously and accurately with good response over a long period of time without being affected by a high oxygen concentration in a measurement gas. The measurement gas is introduced into a first processing zone. A first electrochemical pumping cell is used to lower a partial pressure of oxygen in an atmosphere thereof to a degree sufficient to control a partial pressure of oxygen in a subsequent second processing zone. The gas is introduced into the second processing zone. Oxygen in an atmosphere is pumped out by using a second electrochemical pumping cell so that the partial pressure of oxygen in the atmosphere is controlled to have a low value of partial pressure of oxygen which does not substantially affect measurement of an amount of the measurement gas component. The gas is introduced into a third processing zone. Oxygen produced by reducing or decomposing the measurement gas component is pumped out by using a third electrochemical pumping cell. The amount of the measurement gas component is determined from a detected value of a pumping current flowing through the third electrochemical pumping cell. The amount of the measurement gas component may be also determined by measuring an electromotive force by using an electrochemical sensor cell, in place of the third electrochemical pumping cell.

31 Claims, 7 Drawing Sheets

METHOD AND SENSING DEVICE FOR MEASURING PREDETERMINED GAS COMPONENT IN MEASUREMENT GAS

BACKGROUND OF THE INVENTION

1. Field of the Invention

The present invention relates to a method and a sensing device for measuring a predetermined gas component contained in a measurement gas. In particular, the present invention relates to improvement in methods and various gas sensors for measuring those containing measurement gas components having bonded oxygen. More particularly, the present invention relates to improvement in a sensor adapted for a combustion gas as a measurement gas to measure NOx as a measurement gas component in such a gas, and a method for advantageously measuring NOx in such a gas.

2. Description of the Related Art

Various measuring methods and devices have been proposed for determining the concentration of a desired gas component in a measurement gas. A known method of measuring NOx in a measurement gas such as a combustion gas, for example, employs a sensor comprising a Pt electrode and an Rh electrode formed on an oxygen ion-conductive solid electrolyte such as zirconia. This method utilizes the ability of Rh to reduce NOx so that an electromotive force generated between the two electrodes is measured. However, a problem arises in that such a sensor tends to suffer from an influence of noise, since the electromotive force varies to a great extent depending on a change in concentration of oxygen contained in the combustion gas as the measurement gas, while the electromotive force varies to a small extent in response to a change in concentration of NOx. On the other hand, a reducing gas such as CO is indispensable for such a sensor in order to induce the ability to reduce NOx. However, in general, a large amount of NOx is produced under a combustion condition concerning an excessively small amount of fuel, in which an amount of produced CO is less than the amount of produced NOx, resulting in a drawback that measurement cannot be performed for a combustion gas discharged under such a combustion condition.

Another method of measuring NOx is also known, based on a combination of a set of electrochemical pumping cell and sensing cell including Pt electrodes and oxygen-ion conductive solid electrolyte, and another set of electrochemical pumping cell and sensing cell including Rh electrodes and oxygen-ion conductive solid electrolyte, as disclosed in Japanese Laid-open Patent Publication Nos. 63-38154 and 64-39545. In this method, NOx is measured on the basis of a difference between values of pumping currents. Other methods are disclosed, for example, in Japanese Laid-open Patent Publication Nos. 1-277751 and 2-1543. In one method, two pairs, i.e., a first pair and a second pair of electrochemical pumping cell and sensing cell are prepared. A limiting pumping current is measured by using a sensor comprising the first pair of pumping and sensing cells, under a partial pressure of oxygen at which NOx is not reduced, while a limiting pumping current is measured by using a sensor comprising the second pair of pumping and sensing cells, under a partial pressure of oxygen at which NOx is reduced, so that a difference between the measured limiting pumping currents is determined. In another method, a sensor comprising a pair of pumping cell and sensing cell is used, in which a difference in limiting current is measured by switching the partial pressure of oxygen in a measurement gas between a partial pressure of oxygen at which NOx is reduced and a partial pressure of oxygen at which NOx is not reduced.

In the aforementioned methods of measuring NOx, however, an extremely small part of the value of the limiting current is based on the objective NOx, and the most part of the value of the limiting current is occupied by a current caused by oxygen contained in a large amount in ordinary cases. Therefore, a small current value corresponding to NOx is determined from a difference between two large current values. Accordingly, in the case of the method based on the use of the one set of sensor, problems arise in that the NOx cannot be continuously measured, the operating response is inferior, and the accuracy is inferior. On the other hand, in the case of the method based on the use of the two sets of sensors, an error is likely to occur in a measured value if the oxygen concentration in a measurement gas greatly changes. Therefore, this method cannot be employed in automobile applications, for example, where the oxygen concentration in a measurement gas varies to a large extent. This inconvenience arises from the fact that the dependency of pumping current on oxygen concentration concerning one sensor is different from that concerning the other sensor. In the case of an automobile, for example, the oxygen concentration in exhaust gas is generally several percentages under a running condition of an air/fuel ratio of 20, whereas the NOx concentration is several hundreds of ppm. The concentration of NOx is about $1/100$ of the concentration of oxygen. Therefore, only a slight difference in the dependency of pumping current on oxygen concentration brings about a situation in which a difference in the limiting current value corresponding to a change in oxygen concentration is larger than an amount of change in the limiting current based on NOx to be measured. In addition, if a diffusion rate-determining means formed in the pumping cell is clogged with oil ash in the exhaust gas, the pumping current may be undesirably changed, resulting in reduced accuracy. Further, if the temperature of the exhaust gas greatly varies, a measured value may involve some abnormality. Moreover, a difference in chronological change in any characteristic between the two sensors, if any, may directly lead to measuring errors, resulting in a drawback that the entire system is made undurable for use over a long period of time.

The oxygen present in the measurement gas causes various problems upon measurement of NOx, as described above. The oxygen also causes similar problems, such as reduced measuring accuracy, upon measurement of measurement gas components other than NOx. Accordingly, it has been strongly desired to solve these problems.

In order to solve the problems described above, the present inventors have revealed a new measuring system in Japanese Patent Application No. 7-48551. In this system, a measurement gas component having bonded oxygen, such as NOx, contained in a measurement gas can be measured continuously and accurately with good response over a long period of time without being affected by the oxygen concentration in the measurement gas or any change thereof, by utilizing first and second electrochemical pumping cells arranged in series.

Namely, in the previously proposed new system, a measurement gas containing a measurement gas component having bonded oxygen to be measured is successively introduced from an external measurement gas-existing space into first and second processing zones under predetermined diffusion resistances respectively. At first, in the first processing zone, the partial pressure of oxygen is controlled to have a low value which does not substantially affect measurement of an amount of the measurement gas component by pumping out oxygen in the atmosphere by using a first electrochemical pumping cell. In the second processing zone, the measurement gas component in the atmosphere introduced from the first processing zone is reduced or decomposed. Oxygen produced by the reduction or decomposition is pumped out by the aid of an oxygen-pumping action effected by a second electrochemical pumping cell. Thus a pumping current flowing through the second electrochemical pumping cell is detected to obtain a detected value from which the amount of the measurement gas component in the measurement gas is determined.

However, as a result of further investigation by the present inventors on such a new measuring system, the following problem has been clarified. Namely, the oxygen concentration (partial pressure) in the atmosphere in the first processing zone is controlled by adjusting a pumping voltage of the first electrochemical pumping cell so as to give a constant value of electromotive force detected by a partial oxygen pressure-detecting means (electrochemical sensor cell) arranged for the first processing zone. However, increase in the oxygen concentration in the measurement gas causes change (increase) in the partial pressure of oxygen in the atmosphere to be introduced from the first processing zone to the second processing zone.

The cause of this phenomenon has not been sufficiently elucidated. However, a possible cause is assumed as follows. Namely, increase in the oxygen concentration in the measurement gas may bring about nonuniform distribution of the partial pressure of oxygen in the widthwise direction and the thickness direction in the first processing zone due to shortage of the pumping ability, resulting in change in the partial pressure of oxygen in the atmosphere to be introduced into the second processing zone.

Such shortage of the pumping ability may be counteracted by increasing the pumping ability of the first electrochemical pumping cell. However, such counteraction involves various problems. Specifically, it is assumed to increase the areal size of the pump or increase the temperature of the pump in order to increase the pumping ability. However, increase in the areal size of the pump necessarily involves increase in the areal size of the first processing zone, resulting in a problem that response performance is decreased. Increase in the operation temperature of the pump evokes a problem that reduction of the measurement gas component such as NOx is apt to occur in the first processing zone. In any case, the countermeasure to increase the pumping ability is not effective.

The sensor based on the new measuring system described above involves a problem that measurement of a measurement gas component at a low concentration, for example, measurement of NOx at several ppm gives a pumping current of about several tens of nA detected by the second electrochemical pumping cell, which is small as a detection signal. Further, the sensor also involves a problem that the S/N ratio is considerably lowered due to influence of the change in oxygen concentration as described above. It is noted that measurement of NOx concentration concerning several ppm is greatly affected by occurrence of change in a range of only several ppm in the oxygen concentration in the atmosphere in the second processing zone, caused by change in a range of 0 to 20% in the oxygen concentration in the measurement gas.

SUMMARY OF THE INVENTION

Thus the present invention has been made in order to solve the problems involved in the previously proposed new system for measuring gas components such as NOx, an object of which is to provide a method and a sensing device for measuring a desired gas component, i.e., a gas component containing bonded oxygen in a measurement gas, which makes it possible to perform measurement continuously and accurately with good response over a long period of time without being affected by increase in oxygen concentration in the measurement gas. Another object of the present invention is to provide a method and a sensing device for measuring a predetermined gas component, in which a high S/N ratio can be obtained and a large change in signal can be obtained even when a measurement gas component at a low concentration is measured.

In order to achieve the objects described above, according to a significant aspect of the present invention, there is provided a method of measuring a predetermined measurement gas component in a measurement gas, comprising the steps of introducing the measurement gas containing the measurement gas component having bonded oxygen to be measured, from an external measurement gas-existing space into a first processing zone under a predetermined diffusion resistance, pumping out oxygen in the first processing zone by the aid of an oxygen-pumping action effected by a first electrochemical pumping cell so that a partial pressure of oxygen in an atmosphere in the first processing zone is lowered to a degree sufficient to control a partial pressure of oxygen in a subsequent second processing zone, introducing the atmosphere into the second processing zone under a predetermined diffusion resistance, pumping out oxygen in an atmosphere in the second processing zone by the aid of a second electrochemical pumping cell so that the partial pressure of oxygen in the atmosphere is controlled to have a low value of partial pressure of oxygen which does not substantially affect measurement of an amount of the measurement gas component, introducing the atmosphere into a third processing zone under a predetermined diffusion resistance, reducing or decomposing the measurement gas component introduced from the second processing zone, in an atmosphere in the third processing zone, and pumping out oxygen produced in the reducing or decomposing step, by the aid of a third electrochemical pumping cell so that a pumping current flowing through the third electrochemical pumping cell is detected to obtain a detected value from which the amount of the measurement gas component in the measurement gas is determined.

Therefore, according to the measuring method (first measuring method) of the present invention as described above, the objective amount of the measurement gas component is measured in the third processing zone after the measurement gas is successively introduced into the first and second processing zones. In the first and second processing zones, the measurement gas is subjected to the oxygen-pumping action effected by the first and second electrochemical pumping cells respectively to pump out oxygen. Accordingly, in the first processing zone, nothing is required other than the oxygen concentration is lowered to the degree sufficient to control the partial pressure of oxygen by the aid of the second electrochemical pumping cell in the subsequent second processing zone. In the second processing zone, the value of partial pressure of oxygen, which has been lowered in the first processing zone, is further lowered so that the partial pressure of oxygen may be accurately controlled to have the value of partial pressure of oxygen which does not substantially affect measurement of the amount of the measurement gas component. Therefore, even when the oxygen concentration of the measurement gas is a high concentration from which the partial pressure of oxygen is difficult to be controlled to achieve a desired value by using the second electrochemical pumping cell, the pumping current detected by the third electrochemical pumping cell is not affected by such a high concentration of oxygen. Thus an obtained value accurately corresponds to the amount of the measurement gas component existing in the measurement gas, making it possible to perform accurate measurement.

In the measuring method according to the present invention, it is desirable that the first, second, and third electrochemical pumping cells are heated to a predetermined temperature respectively. Accordingly, an advantage is obtained in that the respective pumping cells perform the pumping action more effectively, for example, even when the temperature of the measurement gas is low or it changes.

In order to achieve the objects described above, according to another significant aspect of the present invention, there is provided a method (second measuring method) of measuring a predetermined measurement gas component in a measurement gas, comprising the steps of introducing the measurement gas containing the measurement gas component having bonded oxygen to be measured, from an external measurement gas-existing space into a first processing zone under a predetermined diffusion resistance, pumping out oxygen in the first processing zone by the aid of an oxygen-pumping action effected by a first electrochemical pumping cell so that a partial pressure of oxygen in an atmosphere in the first processing zone is lowered to a degree sufficient to control a partial pressure of oxygen in a subsequent second processing zone, introducing the atmosphere into the second processing zone under a predetermined diffusion resistance, pumping out oxygen in an atmosphere in the second processing zone by the aid of a second electrochemical pumping cell so that the partial pressure of oxygen in the atmosphere is controlled to have a low value of partial pressure of oxygen which does not substantially affect measurement of an amount of the measurement gas component, introducing the atmosphere into a third processing zone under a predetermined diffusion resistance, reducing or decomposing the measurement gas component introduced from the second processing zone, in an atmosphere in the third processing zone, and outputting, with the use of an electrochemical sensor cell, an electromotive force corresponding to a partial pressure of oxygen in the atmosphere in the third processing zone, defined by oxygen produced in the reducing or decomposing step to obtain a detected output value from which the amount of the measurement gas component in the measurement gas is determined.

In the second measuring method according to the present invention, the partial pressure of oxygen is also controlled in the same manner as performed in the first measuring method described above. Namely, the partial pressure of oxygen in the second processing zone is accurately controlled on the basis of the oxygen-pumping action effected by the first and second electrochemical pumping cells in the first and second processing zones even when the oxygen concentration in the measurement gas is high. In addition, the electromotive force, which is detected according to the output from the electrochemical sensor cell, corresponds to the partial pressure of oxygen in the atmosphere in the third processing zone, defined by oxygen produced by the reduction or decomposition of the measurement gas component in the third processing zone. Accordingly, even when the amount of produced oxygen is minute upon measurement of a measurement gas component having a low concentration, the amount of the measurement gas component can be measured as a large change in electromotive force. Thus a high S/N ratio is realized.

It is also desirable in the second measuring method according to the present invention that the first and second electrochemical pumping cells and the electrochemical sensor cell are heated to a predetermined temperature respectively. Accordingly, the same function and effect as those obtained in the first measuring method can be obtained.

It is advantageous and desirable in the first and second measuring methods according to the present invention that the partial pressure of oxygen in the atmosphere in the first processing zone is controlled by detecting the partial pressure of oxygen in the measurement gas in the first processing zone, changing a voltage of a power source on the basis of an obtained detected value, and controlling the oxygen-pumping action effected by the first electrochemical pumping cell.

In a preferred embodiment of the measuring method according to the present invention, the second and third processing zones are provided in one internal space. In another preferred embodiment, a pumping voltage applied to the second electrochemical pumping cell is substantially the same as a pumping voltage applied to the third electrochemical pumping cell because of the following reason. Namely, it is intended to allow the zero point of the pumping current of the third electrochemical pumping cell (pumping current corresponding to 0 ppm of the measurement gas component) to approach zero. Namely, the pumping voltage, which may be applied to the second and third electrochemical pumping cells, is set so that the current concerning the zero point comes to zero. More preferably, an electromotive force based on the partial pressure of oxygen in the first processing zone is made substantially the same as a pumping voltage applied to the second electrochemical pumping cell because of the following reason. Namely, the smaller the pumping current of the second electrochemical pumping cell is, the smaller the dependency on oxygen is.

According to other significant aspects of the present invention, the following sensing devices for measuring predetermined gas components in measurement gases are also provided, wherein the foregoing measuring methods may be advantageously carried out by using such sensing devices.

One of the sensing devices for measuring predetermined gas components in measurement gases according to the present invention is provided for carrying out the foregoing first measuring method, which lies in a sensing device for measuring an amount of a predetermined measurement gas component in a measurement gas by measuring an amount of oxygen produced by reducing or decomposing the measurement gas component having bonded oxygen in the measurement gas, the sensing device comprising (a) a first processing zone comparted from the outside, the first processing zone communicating with an external measurement gas-existing space, (b) a first diffusion rate-determining means for introducing the measurement gas containing the measurement gas component, from the measurement gas-existing space into the first processing zone under a predetermined diffusion resistance, (c) a first electrochemical pumping cell comprising a first oxygen ion-conductive solid electrolyte and a pair of electrodes provided in contact therewith, for pumping out oxygen from the first processing zone by applying a current between the pair of electrodes so that a partial pressure of oxygen in an atmosphere in the first processing zone is lowered to a degree sufficient to control a partial pressure of oxygen in a subsequent second processing zone, (d) the second processing zone comparted from the outside, the second processing zone communicating with the first processing zone, (e) a second diffusion rate-determining means for introducing the atmosphere in the first processing zone having the lowered partial pressure of oxygen into the second processing zone under a predetermined diffusion resistance, (f) a second electrochemical pumping cell comprising a second oxygen ion-conductive solid electrolyte and a pair of electrodes provided in contact therewith, for pumping out oxygen from the second processing zone by applying a current between the pair of electrodes so that a partial pressure of oxygen in an atmosphere in the second processing zone is controlled to have a low value of partial pressure of oxygen which does not substantially affect measurement of the amount of the measurement gas component, (g) a third processing zone comparted from the outside, the third processing zone communicating with the second processing zone, for reducing or decomposing the measurement gas component in an atmosphere introduced from the second processing zone, (h) a third diffusion rate-determining means for introducing the atmosphere in the second processing zone having the controlled partial pressure of oxygen into the third processing zone under a predetermined diffusion resistance, (i) a third electrochemical pumping cell comprising a third oxygen ion-conductive solid electrolyte and a pair of electrodes provided in contact therewith, for pumping out oxygen produced by reducing or decomposing the measurement gas component in the third processing zone, by applying a current between the pair of electrode, and (j) a current-detecting means for detecting the pumping current allowed to flow by the aid of an pumping action effected by the third electrochemical pumping cell.

In a preferred embodiment, the sensing device according to the present invention further comprises a heating means capable of heating the first, second, and third electrochemical pumping cells to a predetermined temperature respectively.

In another preferred embodiment of the sensing device according to the present invention, a catalyst for reducing or decomposing the measurement gas component to produce oxygen is arranged in the third processing zone.

In still another preferred embodiment of the sensing device according to the present invention, the third oxygen ion-conductive solid electrolyte of the third electrochemical pumping cell constitutes at least a part of a partition wall for comparting the third processing zone, one of the pair of electrodes provided in contact therewith is arranged at a position in the third processing zone, and the electrode arranged in the third processing zone also functions as a catalyst for reducing or decomposing the measurement gas component to produce oxygen. Preferably, the electrode arranged in the third processing zone is composed of a porous cermet comprising a ceramic and a metal capable of reducing or decomposing the measurement gas component having bonded oxygen.

According to the present invention, there is provided another device for carrying out the foregoing second measuring method, which lies in a sensing device for measuring an amount of a predetermined measurement gas component in a measurement gas by measuring an amount of oxygen produced by reducing or decomposing the measurement gas component having bonded oxygen in the measurement gas, the sensing device comprising (a) a first processing zone comparted from the outside, the first processing zone communicating with an external measurement gas-existing space, (b) a first diffusion rate-determining means for introducing the measurement gas containing the measurement gas component, from the measurement gas-existing space into the first processing zone under a predetermined diffusion resistance, (c) a first electrochemical pumping cell comprising a first oxygen ion-conductive solid electrolyte and a pair of electrodes provided in contact therewith, for pumping out oxygen from the first processing zone by applying a current between the pair of electrodes so that a partial pressure of oxygen in an atmosphere in the first processing zone is lowered to a degree sufficient to control a partial pressure of oxygen in a subsequent second processing zone, (d) the second processing zone comparted from the outside, the second processing zone communicating with the first processing zone, (e) a second diffusion rate-determining means for introducing the atmosphere in the first processing zone having the lowered partial pressure of oxygen into the second processing zone under a predetermined diffusion resistance, (f) a second electrochemical pumping cell comprising a second oxygen ion-conductive solid electrolyte and a pair of electrodes provided in contact therewith, for pumping out oxygen from the second processing zone by applying a current between the pair of electrodes so that a partial pressure of oxygen in an atmosphere in the second processing zone is controlled to have a low value of partial pressure of oxygen which does not substantially affect measurement of the amount of the measurement gas component, (g) a third processing zone comparted from the outside, the third processing zone communicating with the second processing zone, for reducing or decomposing the measurement gas component in an atmosphere introduced from the second processing zone, (h) a third diffusion rate-determining means for introducing the atmosphere in the second processing zone having the controlled partial pressure of oxygen into the third processing zone under a predetermined diffusion resistance, (i') an electrochemical sensor cell comprising a fourth oxygen ion-conductive solid electrolyte and a pair of electrodes provided in contact therewith, for outputting an electromotive force corresponding to a partial pressure of oxygen in the atmosphere in the third processing zone, defined by oxygen produced by reducing or decomposing the measurement gas component, and (j') a voltage-detecting means for detecting the electromotive force outputted from the electrochemical sensor cell.

In a preferred embodiment of the second sensing device according to the present invention, the sensing device further comprises a heating means capable of heating the first and second electrochemical pumping cells and the electrochemical sensor cell to a predetermined temperature respectively.

In another preferred embodiment of the sensing device according to the present invention, a catalyst for reducing or decomposing the measurement gas component to produce oxygen is arranged in the third processing zone.

In still another preferred embodiment of the present invention, the fourth oxygen ion-conductive solid electrolyte of the electrochemical sensor cell constitutes at least a part of a partition wall for comparting the third processing zone, one of the pair of electrodes provided in contact therewith is arranged at a position in the third processing zone, and the electrode arranged in the third processing zone also functions as a catalyst for reducing or decomposing the measurement gas component to produce oxygen. Preferably, the electrode arranged in the third processing zone is composed of a porous cermet comprising a ceramic and a metal capable of reducing or decomposing the measurement gas component having bonded oxygen.

In advantageous embodiments, the two sensing devices according to the present invention further comprise a partial oxygen pressure-detecting means for detecting the partial pressure of oxygen in the first processing zone, wherein the partial pressure of oxygen in the first processing zone is controlled by controlling a voltage applied to the first electrochemical pumping cell, on the basis of a value of partial pressure of oxygen detected by the partial oxygen pressure-detecting means.

According to preferred embodiments of the two sensing devices, the second and third processing zones are constructed by one thinly gapped flat space having a predetermined diffusion resistance so that an inlet section of the flat space is used as the second processing zone, and an inner section of the flat space is used as the third processing zone.

According to further advantageous embodiments of the two sensing devices of the present invention, the second diffusion rate-determining means is principally composed of a porous material having a predetermined diffusion resistance, arranged and packed in a communicating passage between the first and second processing zones, and the third diffusion rate-determining means is principally composed of a porous material having a predetermined diffusion resistance, arranged and packed in a communicating passage between the second and third processing zones.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1A:
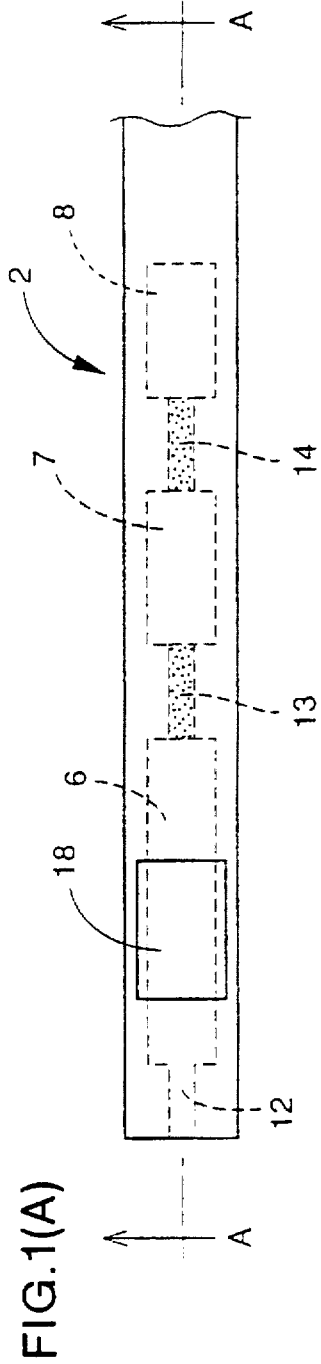
FIG. 1 (A) explanatorily shows a plan view of an embodiment of an NOx sensor according to the sensing device of the present invention, and FIG. 1 (B) explanatorily shows an enlarged view of principal components, taken along a cross section of A—A shown in FIG. 1 (A).

In order to clarify the present invention more specifically, the system of the present invention will be explained in detail below with reference to embodiments concerning measurement of NOx illustrated in the drawings, directed to NOx as a measurement gas component.

Figure 1B:
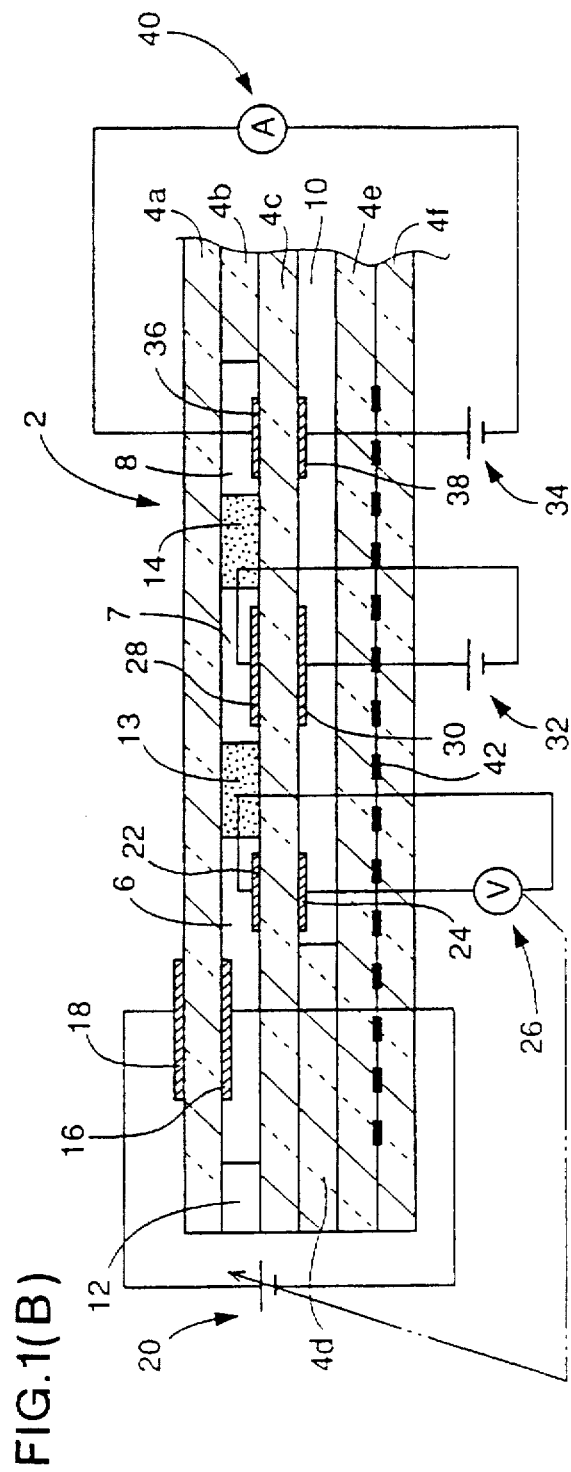

At first, FIG. 1 (A) and FIG. 1 (B) illustrate a representative example of a NOx sensor concerning the sensing device according to the present invention. FIG. 1 (A) shows a plan view of a sensor element of the NOx sensor, and FIG. 1 (B) explanatorily shows an enlarged view of principal components, taken along a cross section of A—A shown in FIG. 1 (A).

With reference to FIG. 1 (A) and FIG. 1 (B), reference numeral 2 indicates a sensor element having a slender and lengthy plate-shaped configuration. As shown in FIG. 1 (B), the sensor element 2 is a plate-shaped object having an integrated structure comprising a plurality of dense and airtight oxygen ion-conductive solid electrolyte layers 4a, 4b, 4c, 4d, 4e, 4f stacked up with each other. Each of the solid electrolyte layers 4a to 4f is formed of a known oxygen ion-conductive solid electrolyte material such as zirconia ceramics. The sensor element 2 having the integrated structure is produced by firing stacked unfired solid electrolyte layers into the integrated structure in the same manner as those hitherto performed.

The sensor element 2 having the integrated structure described above includes a first internal space 6, a second internal space 7, and a third internal space 8 each having a rectangular and plane configuration and individually constructed in a form of being comparted from the outside. The first internal space 6 is located on a distal side of the element, and the third internal space 8 is located on a proximal side of the element. The first, second, and third internal spaces 6, 7, 8 form first, second, and third processing zones, respectively. A reference air-introducing passage 10, which serves as a reference gas-existing space, extends in a longitudinal direction of the sensor element 2. The reference air-introducing passage 10 is provided independently from the first, second, and third internal spaces 6, 7, 8, while overlapping vertically with the first, second, and third internal spaces 6, 7, 8. The reference air-introducing passage 10 is open at the proximal end of the sensor element 2 to make communication with atmospheric air. In this embodiment, the first, second, and third internal spaces 6, 7, 8 are formed such that spaces corresponding thereto formed through the solid electrolyte layer 4b are closed by the upper and lower solid electrolyte layers 4a, 4c. Accordingly, the first, second, and third internal spaces 6, 7, 8 are substantially located on an identical plane. The reference air-introducing passage 10 is formed such that a space corresponding thereto formed through the solid electrolyte layer 4d is closed by the upper and lower solid electrolyte layers 4c, 4e.

A first diffusion rate-determining passage 12, which serves as a first diffusion rate-determining means for allowing the first internal space 6 to communicate with an external measurement gas-existing space, is formed by cutting out the solid electrolyte layer 4b so that the first diffusion rate-determining passage 12 is open at the distal end of the sensor element 2. A measurement gas containing NOx as a measurement gas component is introduced into the first internal space 6 under a predetermined diffusion resistance through the first diffusion rate-determining passage 12. Groove-shaped cutouts are also provided through a portion of the solid electrolyte layer 4b located between the first and second internal spaces 6, 7 and a portion of the solid electrolyte layer 4b located between the second and third internal spaces 7, 8 respectively, where second and third diffusion rate-determining passages 13, 14 are formed, which serve as second and third diffusion rate-determining means respectively. A porous material comprising alumina or the like is arranged and packed in the second and third diffusion rate-determining passages 13, 14. Diffusion resistances of the passages 13, 14 are larger than the diffusion resistance of the first diffusion rate-determining passage 12. An atmosphere in the first internal space 6 is introduced into the second internal space 7 under the predetermined diffusion resistance through the second diffusion rate-determining passage 13. An atmosphere in the second internal space 7 is introduced into the third internal space 8 under the predetermined diffusion resistance through the third diffusion rate-determining passage 14.

A first inner pumping electrode 16, which is composed of a rectangular porous cermet electrode, is provided on a portion of the solid electrolyte layer 4a exposed to the internal space 6, in contact therewith. A first outer pumping electrode 18, which is also composed of a rectangular porous cermet electrode, is provided on an outer surface portion of the solid electrolyte layer 4a corresponding to the first inner pumping electrode 16, in contact therewith. A first electrochemical pumping cell is constructed by the electrodes 16, 18 and the solid electrolyte layer 4a. A desired voltage is applied between the two electrodes 16, 18 of the first electrochemical pumping cell by using an external variable power source 20, and a current is allowed to flow in a direction from the first outer pumping electrode 18 to the first inner pumping electrode 16. Thus oxygen in the atmosphere in the first internal space 6 can be pumped out to the external measurement gas-existing space. The porous cermet electrode comprises a metal such as Pt and a ceramic such as $ZrO_2$. However, the first inner pumping electrode 16 is arranged in the first internal space 6, which contacts with the measurement gas. Therefore, it is necessary for the first inner pumping electrode 16 to use a metal having a weak ability or no ability to reduce the NOx component in the measurement gas. Desirably, the first inner pumping electrode 16 comprises, for example, a cermet of $ZrO_2$ and a Pt-Au alloy.

A measuring electrode 22, which is composed of a porous cermet electrode similarly to the first inner pumping electrode 16, is provided on a portion of the solid electrolyte layer 4c exposed to the internal space 6, in contact therewith. A reference electrode 24, which is composed of a porous cermet electrode similarly to the first outer pumping electrode 18, is provided on a portion of the solid electrolyte layer 4c exposed to the reference air-introducing passage 10, in contact therewith. An electrochemical cell, which serves as a partial oxygen pressure-detecting means, i.e., an electrochemical sensor cell, is constructed by the measuring electrode 22, the reference electrode 24, and the solid electrolyte layer 4c. The partial pressure of oxygen in the atmosphere in the first internal space 6 is detected by measuring an electromotive force generated between the measuring electrode 22 and the reference electrode 24, by using a potentiometer 26, on the basis of a difference in oxygen concentration between the atmosphere in the first internal space 6 and the reference air (atmospheric air) in the reference air-introducing passage 10, as well known in the art. The voltage of the variable power source 20 is controlled on the basis of a value of partial pressure of oxygen in the atmosphere in the first internal space 6, detected by the potentiometer 26. Thus the pumping action of the first electrochemical pumping cell is controlled so that the partial pressure of oxygen in the atmosphere in the first internal space 6 comes to a predetermined low value sufficient to control a partial pressure of oxygen in the subsequent second internal space 7.

A second inner pumping electrode 28, which is composed of a porous cermet electrode similarly to the first inner pumping electrode 16, is provided on the solid electrolyte layer 4c in contact therewith so that the second inner pumping electrode 28 is located in the second internal space 7. A second outer pumping electrode 30, which is composed of a porous cermet electrode similarly to the first outer pumping electrode 18, is provided on a portion of the solid electrolyte layer 4c exposed to the reference air-introducing passage 10, corresponding to the inner pumping electrode 28. A second electrochemical pumping cell is constructed by the inner pumping electrode 28, the outer pumping electrode 30, and the solid electrolyte layer 4c. A desired voltage is applied between the two electrodes 28, 30 of the second electrochemical pumping cell by using an external DC power source 32, and a current is allowed to flow from the second outer pumping electrode 30 to the second inner pumping electrode 28. Thus oxygen in the atmosphere in the second internal space 7 is pumped out to the reference air-introducing passage 10. Accordingly, the partial pressure of oxygen in the atmosphere in the second internal space 7 is controlled to have a low value of partial pressure of oxygen which does not substantially affect measurement of the measurement gas component, in a state in which the measurement gas component (NOx) is not substantially reduced or decomposed.

Further, a rectangular third inner pumping electrode 36 is provided in the third internal space 8, on a portion of the solid electrolyte layer 4c exposed to the third internal space 8, in contact therewith. The third inner pumping electrode 36 is composed of a porous cermet comprising zirconia as a ceramic and Rh which is a metal capable of reducing NOx as the measurement gas component. Thus the third inner pumping electrode 36 functions as a NOx-reducing catalyst capable of reducing NOx existing in an atmosphere in the third internal space 8. On the other hand, a third outer pumping electrode 38 is arranged in the reference air-introducing passage 10, corresponding to the inner pumping electrode 36. A constant voltage is applied by a DC power source 34, between the third inner pumping electrode 36 and the third outer pumping electrode 38. Thus oxygen in the atmosphere in the third internal space 8 is pumped out to the reference air-introducing passage 10. Therefore, in this embodiment, a third electrochemical pumping cell is constructed by the third inner pumping electrode 36, the third outer pumping electrode 38, and the solid electrolyte layer 4c. A pumping current, which flows owing to the pumping action of the electrochemical pumping cell, is detected by an ammeter 40. The constant voltage (DC) power source 34 is capable of applying a voltage of a magnitude conformable to give a limiting current with respect to the pumping of oxygen produced when NOx is decomposed by the third electrochemical pumping cell, under the inflow of NOx restricted by the third diffusion rate-determining passage 14.

A heater 42, which is heated by external power supply, is embedded in the sensor element 2 such that the heater 42 is vertically interposed between the solid electrolyte layers 4e, 4f. Upper and lower surface of the heater 42 are covered with thin layers of ceramic such as alumina, although not shown, in order to obtain electric insulation from the solid electrolyte layers 4e, 4f. In this embodiment, as shown in FIG. 1 (B), the heater 42 is arranged over the entire length ranging from the first internal space 6 to the third internal space 8. Thus the internal spaces 6, 7, 8 are heated to a predetermined temperature respectively. Consequently, the first, second, and third electrochemical pumping cells, as a matter of course, as well as the electrochemical sensor cell are heated to and maintained at the predetermined temperature.

In conformity with the arrangement of the sensor element 2 as described above, its distal end is arranged in the measurement gas-existing space. Accordingly, the measurement gas is introduced into the first internal space 6 under the predetermined diffusion resistance through the first diffusion rate-determining passage 12 provided in the sensor element 2. The measurement gas introduced into the first internal space 6 undergoes the oxygen-pumping action evoked by applying a predetermined voltage between the two electrodes 16, 18 which constitute the first electrochemical pumping cell so that the partial pressure of oxygen is controlled to have a predetermined value, for example, $10^{-10}$ atm.

In order to control the partial pressure of oxygen in the atmosphere in the first internal space 6 to have the predetermined value, a technique is adopted on the basis of the well known Nernst equation. Namely, the electromotive force between the measuring electrode 22 and the reference electrode 24 of the electrochemical sensor cell is measured by using the potentiometer 26. The voltage (variable power source 20) applied between the two electrodes 16, 18 of the first electrochemical pumping cell is controlled so that the electromotive force is, for example, 430 mV (700° C.). Thus the partial pressure of oxygen is controlled to have the objective value of $10^{-10}$ atm. Namely, the voltage of the first electrochemical pumping cell is controlled so that the electromotive force corresponds to a difference between a desired oxygen concentration in the first internal space 6 and an oxygen concentration in the reference air. The first diffusion rate-determining passage 12 serves to reduce the amount of oxygen in the measurement gas diffusing and flowing into the measuring space (first internal space 6) when the voltage is applied to the first electrochemical pumping cell so that the current flowing through the first electrochemical pumping cell is suppressed.

A state of partial pressure of oxygen, in which NOx in the atmosphere is not reduced by the inner pumping electrode 16 and the measuring electrode 22, for example, a state of partial pressure of oxygen, in which the reaction: NO→½N₂+½O₂ does not take place, is established in the first internal space 6 even under a heated condition caused by heating by the external measurement gas and the heater 42. If NOx in the measurement gas (or in the atmosphere) is reduced in the first internal space 6, it is impossible to accurately measure NOx in the subsequent third internal space 8. In this context, it is necessary to establish the state in which NOx is not reduced by any component (any metal component of the inner pumping electrode 16 and the measuring electrode 22 in this embodiment) which may concern reduction of NOx.

Accordingly, the partial pressure of oxygen in the atmosphere in the first internal space 6 is intended to be controlled to have the low value of partial pressure of oxygen which does not substantially affect measurement of NOx, by operating the pumping action of the first electrochemical pumping cell arranged as described above. In other words, the voltage of the variable power source 20 is intended to be adjusted so that the voltage of the measuring electrode 22 detected by the electrochemical sensor cell is constant. However, under the intended control or adjustment as described above, if the oxygen concentration in the measurement gas greatly changes, for example, if the oxygen concentration in the measurement gas changes in a range of 0 to 20%, a slight change occurs in partial pressure of oxygen not only in the atmosphere in the subsequent internal space 7 into which the atmosphere in the first internal space 6 is introduced, but also in the atmosphere in the following internal space 8. As estimated above, such a change may be caused by the following reason. Namely, increase in oxygen concentration in the measurement gas may bring about distribution of oxygen concentration in the widthwise direction and the thickness direction of the internal space 6 over the measuring electrode 22, and the distribution of oxygen concentration may change depending on the oxygen concentration in the measurement gas. This situation can be confirmed by observing the change in the electromotive force generated between the electrodes 28, 30 and the change in the electromotive force generated between the electrodes 36, 38 on condition that only the first electrochemical pumping cell is operated, and the second and third electrochemical pumping cells are not operated (to which no pumping current is applied). An exemplary result is shown in FIG. 2.

Figure 2:
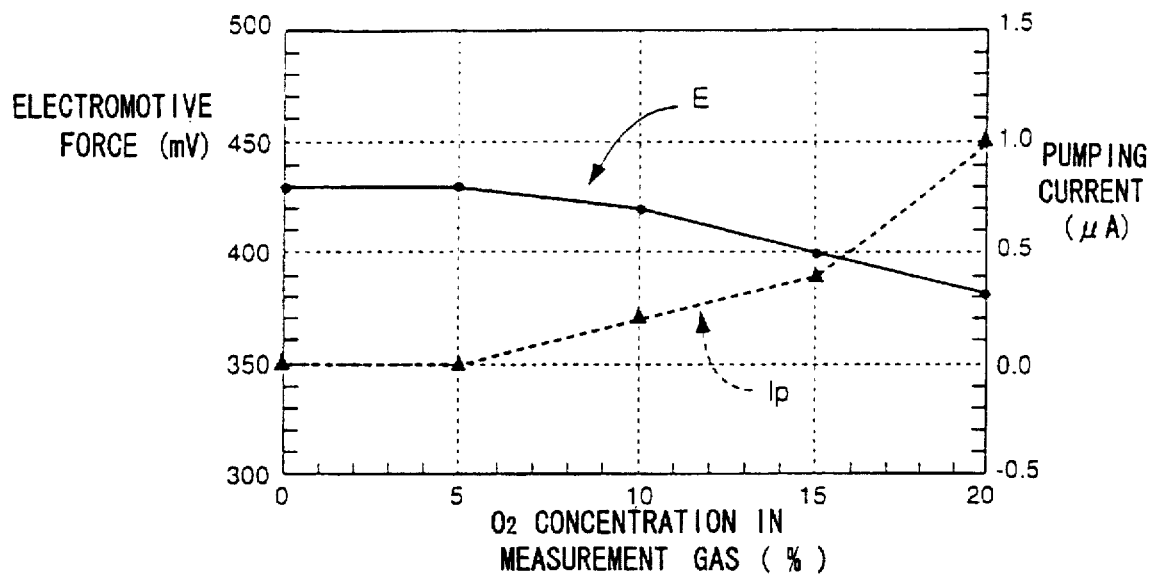
FIG. 2 shows a graph exemplarily illustrating change in electromotive force and change in pumping current of the NOx sensor with respect to the oxygen concentration in a measurement gas.

FIG. 2 shows change in partial pressure of oxygen in the third internal space 8 obtained when the oxygen concentration of the measurement gas is changed in a range of 0 to 20%, i.e., the change in electromotive force (E) generated between the third inner pumping electrode 36 and the third outer pumping electrode 38, and the change in pumping current (Ip) obtained when a voltage $V_3$=430 mV is applied by using the DC power source 34. FIG. 2 shows the fact that the partial pressure of oxygen in the atmosphere in the third internal space 8 gradually increases if the oxygen concentration in the measurement gas exceeds 5%. The result shown in FIG. 2 was obtained under the following condition. Namely, a cermet electrode comprising a Pt alloy containing 1% Au, and $ZrO_2$ in a volume ratio of 60:40 was used as the first inner pumping electrode 16 in the first internal space 6. The temperature was set to be 700° C. The first electrochemical pumping cell was operated to perform the pumping action by controlling the voltage of the variable power source 20 so that the voltage of the measuring electrode 22 was 430 mV.

As described above, even if the oxygen in the atmosphere in the first internal space 6 is pumped out by using the first electrochemical pumping cell (4a, 16, 18), the partial pressure of oxygen in the atmosphere introduced from the first internal space 6 into the second internal space 7 gradually increases due to the increase in oxygen concentration in the measurement gas. Therefore, in such a situation, the zero point of the pumping current value varies depending on the oxygen concentration in the measurement gas even if it is intended to measure the amount of NOx on the basis of the pumping current obtained by pumping out oxygen produced by reducing NOx in the atmosphere, by using the electrochemical pumping cell. For this reason, it is difficult to accurately measure the amount of NOx.

Accordingly, in the embodiment shown in FIG. 1 (A) and FIG. 1 (B), the second electrochemical pumping cell (4c, 28, 30) is provided for the second internal space 7 so that the partial pressure of oxygen in its internal atmosphere always comes to a constant and low value of partial pressure of oxygen. The pumping action of the second electrochemical pumping cell (4c, 28, 30) enables the partial pressure of oxygen in the atmosphere in the second internal space 7 to always have the constant and low value even if the partial pressure of oxygen introduced from the first internal space 6 changes depending on the oxygen concentration of the measurement gas. Thus the partial pressure of oxygen is controlled to have the low value which does not substantially affect measurement of NOx.

A state of partial pressure of oxygen, in which NOx in the atmosphere is not reduced by the second inner pumping electrode 28, is also established in the second internal space 7 similarly to the first internal space 6, under a heated condition caused by heating by the external measurement gas and the heater 42. Accordingly, an electrode material having no ability or a weak ability to reduce the measurement gas is also used for the second inner pumping electrode 28 similarly to the first inner pumping electrode 16 and the measuring electrode 22.

Figure 3:
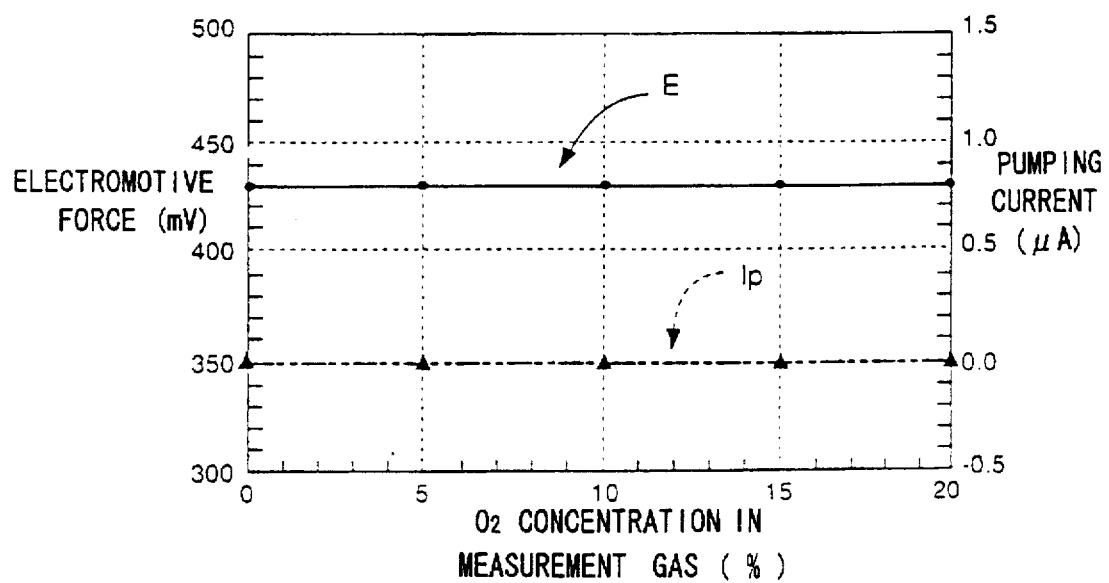
FIG. 3 shows a graph exemplarily illustrating change in electromotive force and change in pumping current with respect to the oxygen concentration in a measurement gas, concerning the sensing device according to the present invention.

FIG. 3 shows a result of operation similar to that performed in FIG. 2, by applying a voltage of 430 mV from the DC power source 32 to the second electrochemical pumping cell to effect the pumping action. As clarified from FIG. 3, it is understood that owing to the pumping action of the second electrochemical pumping cell, the partial pressure of oxygen in the atmosphere in the third internal space 8 scarcely changes, and the pumping current (Ip) is not affected by the oxygen concentration of the measurement gas.

The measurement gas, which has its partial pressure of oxygen controlled in the second internal space 7 as described above, is introduced into the third internal space 8 through the third diffusion rate-determining passage 14 under the predetermined diffusion resistance. The measurement gas introduced into the third internal space 8 undergoes the oxygen-pumping action by applying a predetermined voltage, for example, 430 mV (700° C.) between the third inner pumping electrode 36 and the third outer pumping electrode 38 which constitute the third electrochemical pumping cell, in a direction to pump out oxygen from the third internal space 3 to the reference air-introducing passage 10. Accordingly, the oxygen concentration is further decreased in the third internal space 8, especially at the interface of three phases on the third inner pumping electrode 36. Thus the oxygen concentration comes to $10^{-10}$ atm, which is controlled to establish a state in which NOx is reduced, for example, a state in which the reaction: NO→½$N_2$+½$O_2$ is brought about around the inner pumping electrode 36 which also functions as a catalyst for reducing NOx. At this time, the current flowing through the third electrochemical pumping cell comes to a value which is proportional to a sum of the oxygen concentration in the atmosphere introduced into the third internal space 8, that is the oxygen concentration in the atmosphere in the second internal space 7, and the oxygen concentration produced by reducing NOx by the aid of third inner pumping electrode 36. However, the oxygen concentration in the atmosphere in the second internal space 7 is controlled to be constant by the second electrochemical pumping cell. Accordingly, the current flowing through the third electrochemical pumping cell is proportional to the concentration of NOx. The concentration of NOx corresponds to an amount of diffusion of NOx restricted by the third diffusion rate-determining passage 14. Thus the concentration of NOx can be measured.

For example, it is assumed that the partial pressure of oxygen in the second internal space 7 controlled by the second electrochemical pumping cell is 0.02 ppm, and the concentration of NO as a NOx component in the measurement gas is 100 ppm. On this assumption, the oxygen concentration produced by reducing NO is 50 ppm which is added to the oxygen concentration of 0.02 ppm in the atmosphere in the second internal space 7 to obtain a sum of 50.02 ppm. Thus a current corresponding to the sum of 50.02 ppm is allowed to flow. Therefore, the value of the pumping current flowing through the third electrochemical pumping cell mostly represents the amount obtained by reduction of NO. Accordingly, there is no dependency on the oxygen concentration in the measurement gas.

Figure 4:
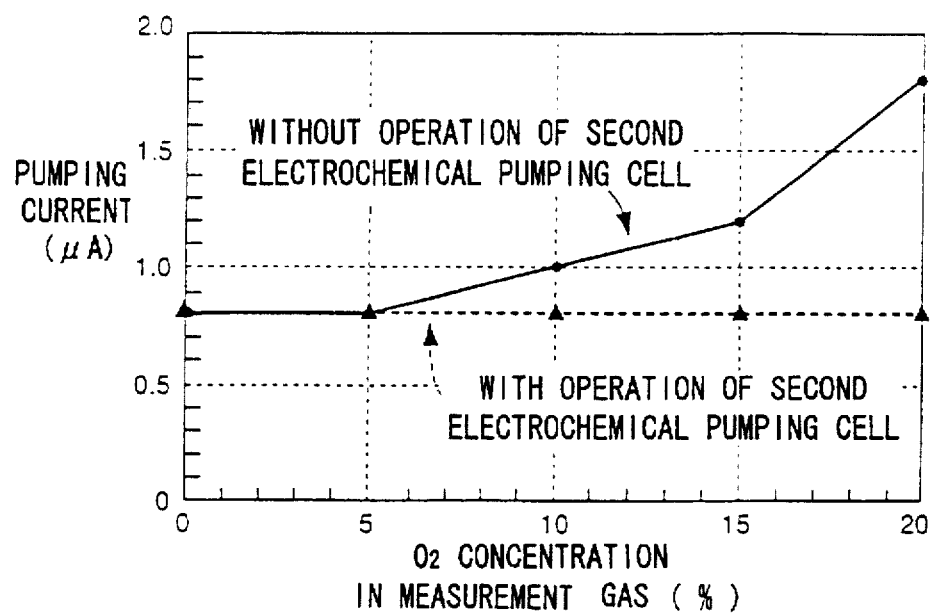
FIG. 4 shows a graph exemplarily illustrating relationships between the oxygen concentration in a measurement gas and the pumping current with or without operation of a second electrochemical pumping cell.

FIG. 4 shows change in pumping current (Ip) flowing through the third electrochemical pumping cell, obtained when the concentration of NO as the NOx component was fixed at 100 ppm, and the oxygen concentration in the measurement gas was changed in a range of 0 to 20% by using $N_2$ as a carrier gas. The pumping voltage was set to be 430 mV in any of the first, second, and third electrochemical pumping cell. As clarified from the result shown in FIG. 4, no change is observed in the pumping current value (Ip) concerning decomposition of NO, even if the oxygen concentration in the measurement gas changes, when the second electrochemical pumping cell is operated so that the partial pressure of oxygen in the atmosphere in the second internal space 7 is controlled to have a constant value. Therefore, an accurate pumping current value (Ip) corresponding to the NO concentration is obtained irrelevant to any change in oxygen concentration in the measurement gas. On the contrary, the pumping current value (Ip) flowing through the third electrochemical pumping cell gradually increases as the oxygen concentration in the measurement gas increases when the second electrochemical pumping cell is not subjected to the pumping operation. Accordingly, it is understood that it is difficult to accurately determine the NO concentration from the pumping current value (Ip).

Figure 5:
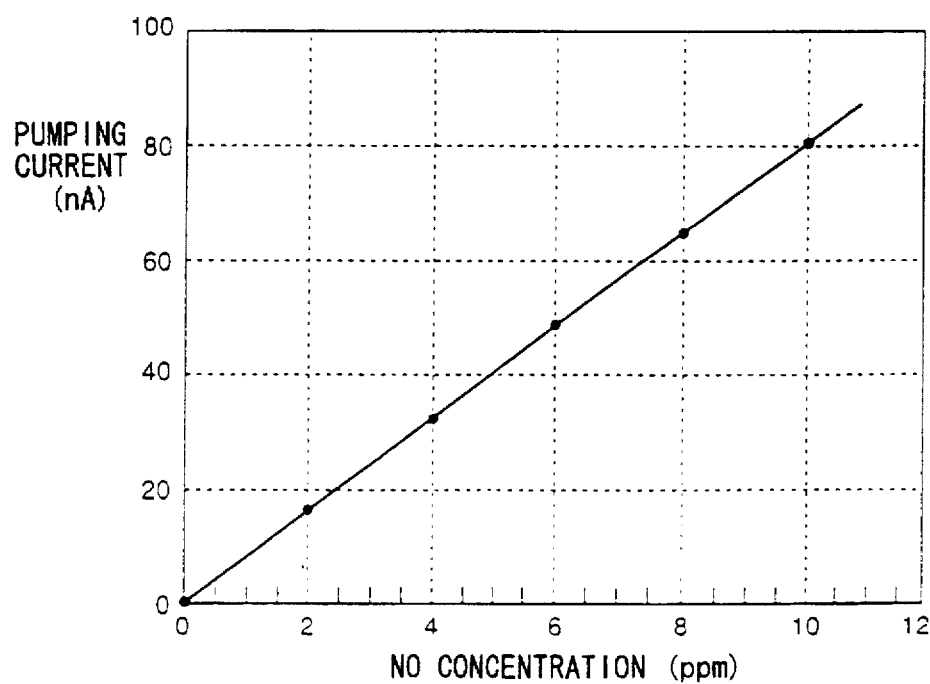
FIG. 5 shows a graph exemplarily illustrating a relationship between the oxygen concentration in a measurement gas and the pumping current, obtained by using the sensing device according to the present invention.

In addition, the S/N ratio is increased by eliminating the influence exerted by the oxygen concentration in the measurement gas as described above. Therefore, even a measurement gas component having a low concentration can be measured. FIG. 5 shows change in pumping current (Ip) flowing through the third electrochemical pumping cell, obtained when the oxygen concentration was 5%, and the NO concentration in the measurement gas was changed in a range of 0 to 10 ppm by using $N_2$ as a carrier gas under a condition in which the first, second, and third electrochemical pumping cells were subjected to pumping operation at a pumping voltage of 430 mV respectively. As clarified form FIG. 5, even in the case of a low concentration of NO of not more than 10 ppm, although the detected pumping current value is small, the obtained pumping current corresponds to the NO concentration. Accordingly, it is understood that it is possible to measure the NO component at such a low concentration.

In the foregoing embodiment, any one of the first and second inner pumping electrodes 16, 28 and the measuring electrode 22, arranged in the first internal space 6 and the second internal space 7, is required not to reduce or decompose the measurement gas component (NOx) in each of the atmospheres at the ambient temperature and the controlled partial pressure of oxygen in each of the internal spaces. Accordingly, those usable include electrode metals such as Au and Ni having no ability or a weak ability to reduce or decompose the measurement gas component. Those advantageously usable include, for example, cermet electrodes comprising the metal described above, and cermet electrodes obtained by using an alloy prepared by adding a metal having no catalytic ability such as Au and Ni described above to a noble metal such as Pt, Pd, and Rh. Desirably, the third inner pumping electrode 36 arranged in the third internal space 8 is a cermet electrode composed of, for example, Rh or Pt capable of reducing or decomposing the measurement gas component (NOx) in the atmosphere at the environmental temperature and the partial pressure of oxygen in the third internal space 8. It is of course possible to use, as the third inner pumping electrode 36, those obtained by arranging and stacking, on an ordinary electrode, an Rh or Pt electrode, or a catalyst material comprising a NOx-reducing metal carried on a ceramic porous material such as alumina, and those obtained by arranging an Rh catalyst electrode on a Pt electrode.

In any case, the respective electrodes provided for the NOx sensor described above, especially the inner pumping electrodes 16, 28, 36 and the measuring electrode 22 arranged in the respective internal spaces are desirably cermet electrodes composed of an electrode metal and an appropriate ceramic. In particular, as exemplified above, in the case of the use of the third inner pumping electrode 36 which also functions as a NOx-reducing catalyst, it is desirable to use a porous cermet electrode comprising a ceramic and a known metal capable of reducing NOx such as Rh and Pt. The NOx-reducing catalyst may be provided in the close vicinity of the third inner pumping electrode 36 of the third electrochemical pumping cell for pumping out oxygen in the third internal space 8. Alternatively, a porous alumina, on which a NOx-reducing catalyst comprising, for example, Rh is carried, may be stacked on the third inner pumping electrode 36 by means of printing or the like to form a NOx-reducing catalyst layer on the electrode.

It is needless to say that the sensing device according to the present invention should not be interpreted such that the device is limited to only the aforementioned structure. Any one of various forms and structures, as previously clarified by the present inventors in Japanese Patent Application No. 7-48551, may be appropriately adopted. One modified embodiment of such sensing devices is shown in FIG. 6.

Figure 6:
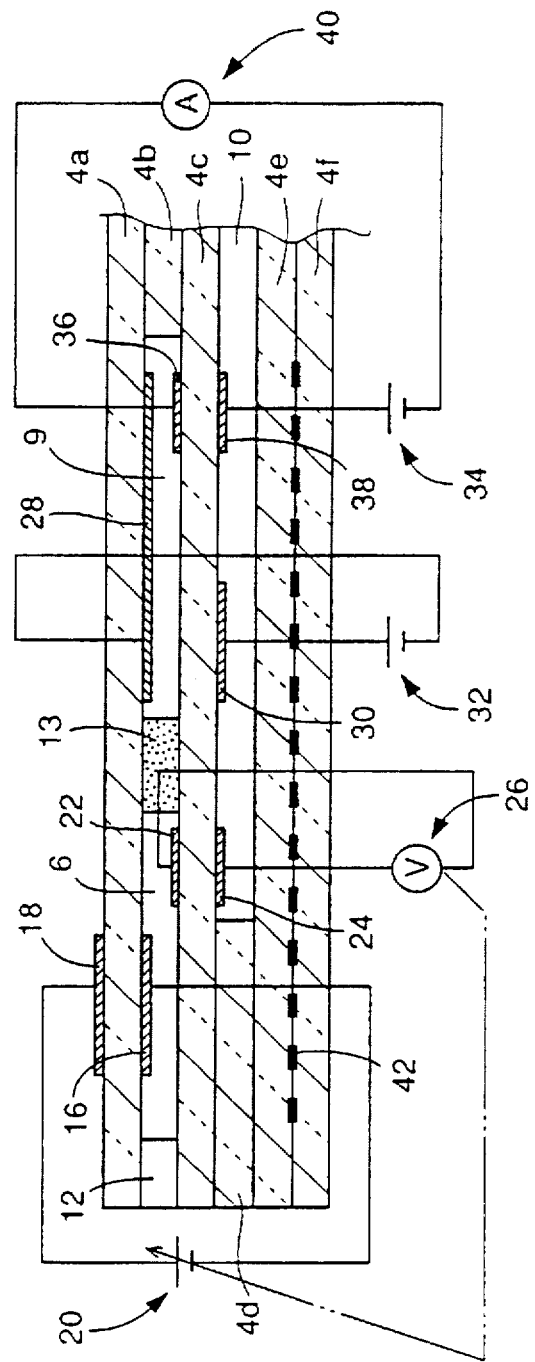
FIG. 6 explanatorily shows a cross-sectional view corresponding to FIG. 1 (B), illustrating a modified embodiment of the sensing device according to the present invention.

The modified embodiment shown in FIG. 6 is different from the foregoing embodiment, which is specifically characterized in that the second internal space 7 and the third internal space 8 are integrated to provide a combined internal space 9 comprising one thinly gapped flat space, and a second inner pumping electrode 28 and a third inner pumping electrode 36 are arranged therein. Namely, the combined internal space 9 includes the second processing zone and the third processing zone. The measurement gas, which is introduced from the first internal space 6 through the second diffusion rate-determining passage 13, undergoes the oxygen-pumping action effected by a second electrochemical pumping cell constructed by the second inner pumping electrode 28, the second outer pumping electrode 30, and the solid electrolyte layers 4a, 4b, 4c arranged on an inlet side of the combined internal space 9. Thus the partial pressure of oxygen is controlled to have a low and constant value. The measurement gas diffuses under a predetermined diffusion resistance defined by the thinly gapped flat space of the combined internal space 9, and it arrives at the third electrochemical pumping cell arranged at an inner section of the combined internal space 9 where NOx as the measurement gas component is reduced by the third inner pumping electrode 36. Oxygen is pumped out from the third inner pumping electrode 36 to the third outer pumping electrode 38. Thus the pumping current (Ip) flowing through the third electrochemical pumping cell is detected by the ammeter 40.

Figure 7:
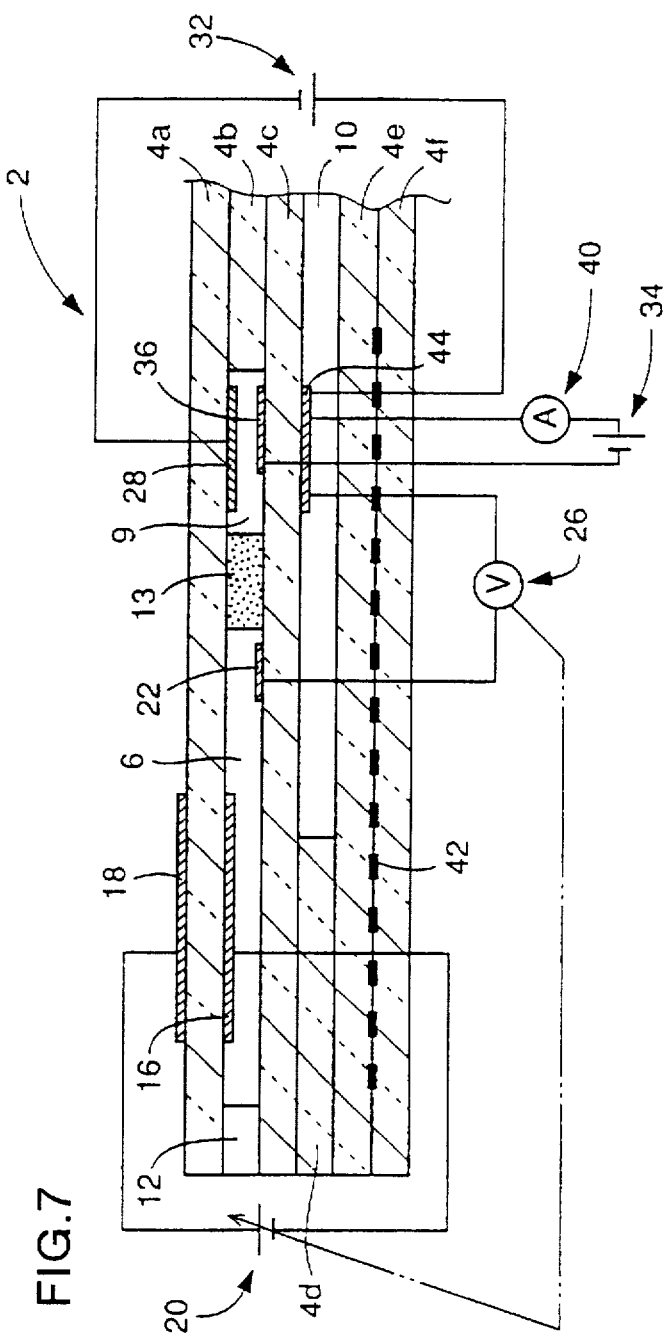
FIG. 7 explanatorily shows a cross-sectional view corresponding to FIG. 1 (B), illustrating another modified embodiment of the sensing device according to the present invention.

Another modified embodiment shown in FIG. 7 is different from the embodiment shown in FIG. 6, which is characterized in that the reference electrode 24 of the electrochemical sensor cell arranged in the reference air-introducing passage 10, the second outer pumping electrode 30 of the second electrochemical pumping cell, and the third outer pumping electrode 38 of the third electrochemical pumping cell are constructed by a common electrode 44.

The sensor structure of this embodiment is similar to the foregoing embodiment shown in FIG. 6 in that one combined internal space 9 is used to construct the second and third processing zones.

In the foregoing embodiments, the oxygen, which is produced by reducing or decomposing the measurement gas component such as NOx in the third processing zone, is subjected to the pumping operation effected by the third electrochemical pumping cell to obtain a pumping current value from which the concentration of the measurement gas component is determined. However, such a pumping current value decreases in proportion to decrease in concentration of the measurement gas component. Accordingly, a precision ammeter is required to detect such a small pumping current value. In order to measure a measurement gas component having such a low concentration contained in a measurement gas, the present invention advantageously adopts the following method and device.

Namely, this embodiment comprises the steps of reducing or decomposing the measurement gas component introduced from the second processing zone, in an atmosphere in the third processing zone, and detecting, with the use of an output from an electrochemical sensor cell, an electromotive force corresponding to a partial pressure of oxygen in the atmosphere in the third processing zone, defined by oxygen produced in the reducing or decomposing step to obtain a detected value from which the amount of the measurement gas component in the measurement gas is determined. An example is shown in FIG. 8.

Figure 8:
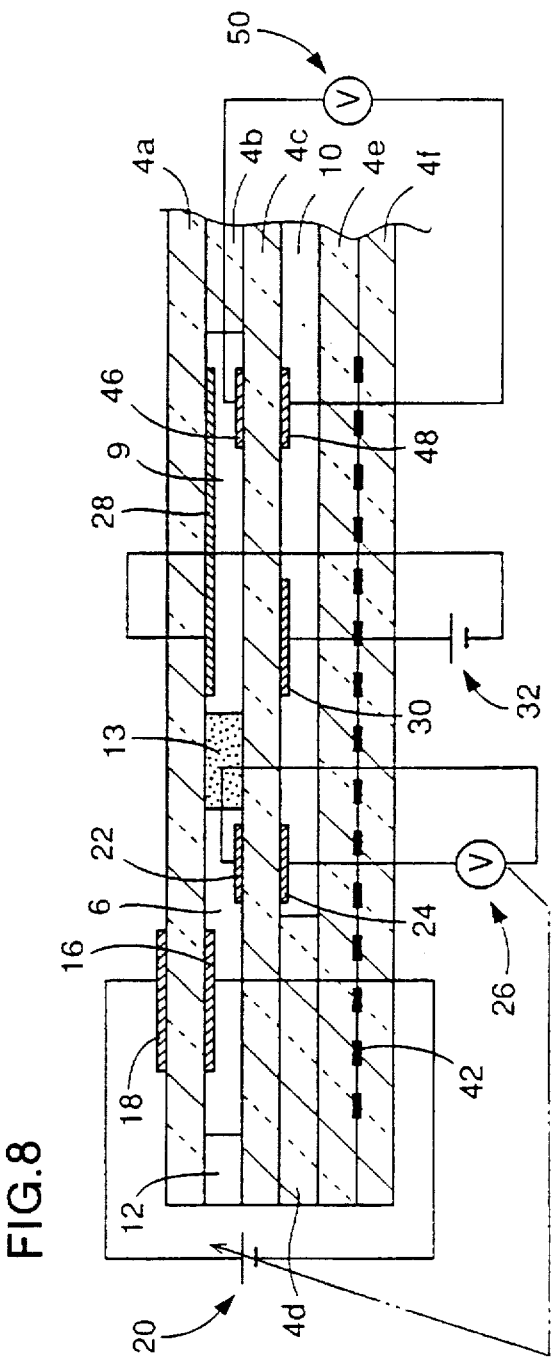
FIG. 8 explanatorily shows a cross-sectional view corresponding to FIG. 1 (B), illustrating another embodiment of the sensing device according to the present invention.

A sensing device (sensor) shown in FIG. 8 adopts a structure equivalent to that in FIG. 6 described above, which is characterized in that in place of the third electrochemical pumping cell shown in FIG. 6, an electrochemical sensor cell is provided, while adopting a similar arrangement of electrodes. In this electrochemical sensor cell, a measuring electrode 46 is provided and exposed to an inner side of a combined internal space 9. A reference electrode 48 is provided on the solid electrolyte layer 4c so that the reference electrode 48 is exposed to the inside of the reference air-introducing passage 10. The electrochemical sensor cell, which serves as a partial oxygen pressure-detecting means, is constructed by the measuring electrode 46, the reference electrode 48, and the solid electrolyte layer 4c. As well known, an electromotive force, which is generated between the measuring electrode 46 and the reference electrode 48, is outputted on the basis of a difference in oxygen concentration between an atmosphere around the measuring electrode 46 and an atmosphere around the reference electrode 48. The electromotive force is measured by a potentiometer 50. Thus a partial pressure of oxygen in the atmosphere around the measuring electrode 46, in other words, a partial pressure of oxygen defined by oxygen produced by reducing or decomposing the measurement gas component (NOx) is detected.

In this sensing device, it is assumed that when NO as NOx as the measurement gas is 0 ppm, the oxygen concentration in the atmosphere in the first internal space 6 is controlled to have a value ($10^{-10}$ atm) corresponding to a pumping voltage of 430 mV of the first electrochemical pumping cell. On this assumption, the oxygen concentration in the atmosphere in the combined internal space 9 is also $10^{-10}$ atm, and the electromotive force between the measuring electrode 46 and the reference electrode 48 is 430 mV, if the oxygen in the atmosphere in the combined internals space 9 is not pumped out. For example, it is assumed that 10 ppm of NO exists in the measurement gas. The measuring electrode 46 also functions as a NOx-reducing catalyst in the same manner as the third inner pumping electrode 36 of the third electrochemical pumping cell described above. Accordingly, reduction of NO is evoked on the measuring electrode 46, and the oxygen concentration in the atmosphere around the measuring electrode 46 increases. Thus the electromotive force is lowered. The degree of decrease in electromotive force represents the NO concentration. In other words, the electromotive force, which is outputted by the electrochemical sensor cell constructed by the measuring electrode 46, the reference electrode 48, and the solid electrolyte layer 4c, represents the NO concentration in the measurement gas.

Stability of the electromotive force obtained when the NO concentration in the measurement gas is zero is extremely important for the measurement operation. As described previously with reference to FIG. 2, the electromotive force decreases as the oxygen concentration in the measurement gas increases. The electromotive force greatly changes in a range of 50 mV, from 430 mV obtained when the oxygen concentration is 0% to 380 mV obtained when the oxygen concentration is 20%.

However, in the present invention, owing to the pumping action effected by the second electrochemical pumping cell, especially in the embodiment shown in FIG. 8, owing to the pumping action effected by the electrochemical pumping cell comprising the second inner pumping electrode 28, the second outer pumping electrode 30, and the solid electrolyte layers 4a, 4b, 4c, the electromotive force scarcely changes even when the oxygen concentration in the measurement gas changes in a range of 0 to 20% as shown in FIG. 3. Accordingly, the electromotive force corresponding to the amount of NO in the measurement gas is generated between the measuring electrode 46 and the reference electrode 48 which constitute the electrochemical sensor cell. An accurate amount of NO can be determined by detecting the generated electromotive force.

Figure 9:
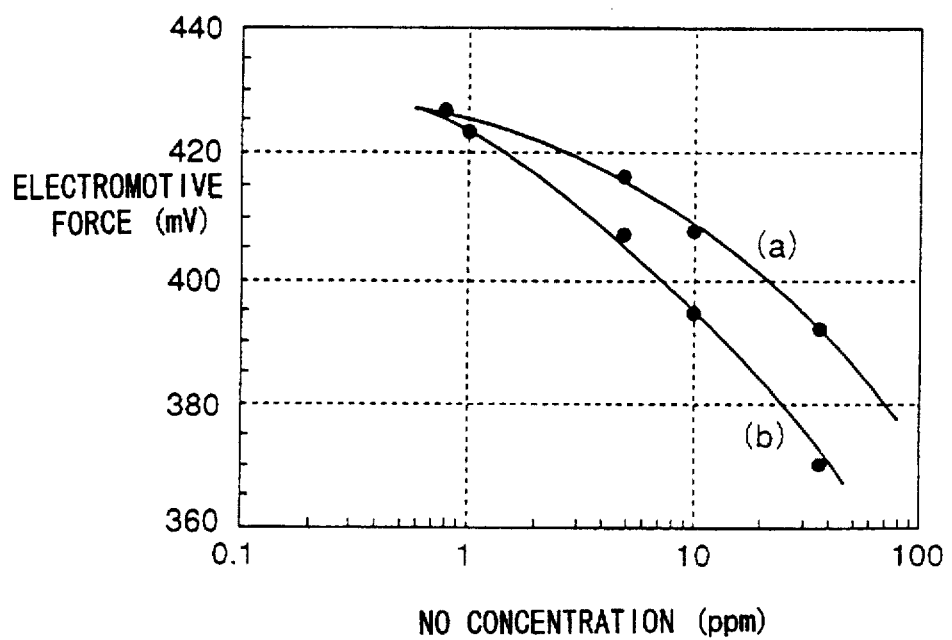
FIG. 9 shows a graph exemplarily illustrating relationships between the NO concentration in a measurement gas and the electromotive force, obtained according to the present invention.

The sensing device shown in FIG. 8 was used under the following condition. Namely, the pumping voltage of the first and second electrochemical pumping cells was 430 mV. The partial pressure of oxygen in the atmospheres in the first internal space 6 and the combined internal space 9 was controlled to be $10^{-10}$ atm. In this state, NO as a NOx component in a measurement gas comprising 5% $O_2$ in a carrier gas of $N_2$ was changed in a range of 0.8 to 40 ppm. The change in electromotive force between the measuring electrode 46 and the reference electrode 48, obtained under this condition, is shown in FIG. 9. As clarified from the result shown in FIG. 9, the electromotive force changes in a range of about 50 mV, in a range of NO concentration of 1 to 10 ppm. Accordingly, a large change in signal can be detected by the potentiometer 50 even when the NO concentration in the measurement gas is low.

When the NO concentration is determined by measuring the electromotive force as described above, it is possible to select the sensitivity to NO and the measuring range by controlling the diffusion resistance concerning the measuring electrode 46. As for the result shown in FIG. 9, a curve (a) represents a case of the use of a diffusion resistance of the measuring electrode 46 itself comprising a porous cermet having an electrode thickness of 20 μm and a porosity of 20%. A curve (b) represents a case of the use of a porous zirconia layer having a porosity of 10% and a thickness of 20 μm provided on the measuring electrode shown by the curve (a), providing a higher sensitivity as compared with the curve (a). Accordingly, the sensitivity to NO is increased by increasing the diffusion resistance by providing, for example, a porous diffusion rate-determining section such as a porous alumina layer and a porous zirconia layer stacked on the measuring electrode 46. However, it is difficult to perform measurement in a high concentration region. $O_2$ produced by reduction on the electrode is apt to remain in the electrode area, and the oxygen concentration is apt to increase. Therefore, the change in electromotive force becomes large. However, the oxygen concentration in the electrode area is apt to increase due to $O_2$ produced by reduction. For this reason, reduction does not occur if the oxygen concentration exceeds a certain level. Accordingly, it is difficult to perform measurement in a high concentration region. Therefore, the sensitivity and the measuring range should be determined by appropriately setting the diffusion resistance depending on the feature of a region in which the NO concentration is measured.

In any of the foregoing embodiments, NOx is a target as the measurement gas component. Of course, it is needless to say that the present invention may be effectively adapted to measurement of other gas components containing bonded oxygen other than NOx, such as $H_2O$ and $CO_2$, which is affected by oxygen existing in the measurement gas.

It is needless to say that the present invention may be carried out in various altered, corrected, and improved forms on the basis of the knowledge of those skilled in the art. It should be understood that any of such forms belongs to the category of the present invention, within a range without deviating from the spirit of the present invention.

As clarified from the foregoing explanation, according to the method and the sensing device for measuring a predetermined gas component in a measurement gas concerning the present invention, a stable pumping current or a stable electromotive force corresponding to a concentration of an intended measurement gas can be obtained without being affected at all by the oxygen concentration in the measurement gas or any change thereof, especially even when the oxygen concentration in the measurement gas is high. Thus the concentration of the measurement gas component can be accurately measured. Further, it is possible to perform measurement continuously and accurately with good response over a long period of time.

According to the present invention, the influence exerted by the oxygen concentration in the measurement gas is dissolved. Thus the S/N ratio is increased, making it possible to perform measurement even when a measurement gas component has a low concentration. Especially, a large change in electromotive force, i.e., a large change in signal is obtained even when a measurement gas component has a low concentration, by detecting an electromotive force corresponding to a partial pressure of oxygen in an atmosphere, defined by oxygen produced by reducing or decomposing the measurement gas component having bonded oxygen, thus exhibiting the feature that accurate measurement is easily performed.

What is claimed is:

1. A method of measuring a predetermined measurement gas component in a measurement gas, comprising the steps of:

introducing said measurement gas containing said measurement gas component having bonded oxygen to be measured, from an external measurement gas space into a first processing zone under a predetermined diffusion resistance;

pumping out oxygen in said first processing zone by the aid of an oxygen-pumping action effected by a first electrochemical pumping cell so that a partial pressure of oxygen in an atmosphere in said first processing zone is lowered to a degree sufficient to control a partial pressure of oxygen in a subsequent second processing zone;

introducing said atmosphere into said second processing zone under a predetermined diffusion resistance, said second processing zone being in serial communication with said first processing zone;

pumping out oxygen in an atmosphere in said second processing zone by the aid of a second electrochemical pumping cell so that said partial pressure of oxygen in said atmosphere is controlled to have a low value of partial pressure of oxygen which does not substantially affect measurement of an amount of said measurement gas component;

introducing said atmosphere into a third processing zone under a predetermined diffusion resistance, said third processing zone being in serial communication with said second processing zone;

reducing or decomposing said measurement gas component introduced from said second processing zone, in an atmosphere in said third processing zone; and pumping out oxygen produced in said reducing or decomposing step, by the aid of a third electrochemical pumping cell so that a pumping current flowing through said third electrochemical pumping cell is detected to obtain a detected value from which said amount of said measurement gas component in said measurement gas is determined.

2. The method according to claim 1, wherein said first, second, and third electrochemical pumping cells are heated to a predetermined temperature respectively.

3. The method according to claim 1, wherein said partial pressure of oxygen in said atmosphere in said first processing zone is controlled by detecting said partial pressure of oxygen in said measurement gas in said first processing zone, changing a voltage of a power source on the basis of an obtained detected value, and controlling said oxygen-pumping action effected by said first electrochemical pumping cell.

4. The method according to claim 1, wherein said second and third processing zones are provided in the shared confined structure of one internal space.

5. The method according to claim 1, wherein a pumping voltage applied to said second electrochemical pumping cell is substantially the same as an electromotive force based on said partial pressure of oxygen in said atmosphere in said first processing zone.

6. The method according to claim 1, wherein a pumping voltage applied to said third electrochemical pumping cell is substantially the same as a pumping voltage applied to said second electrochemical pumping cell.

7. The method according to claim 1, wherein said measurement gas component having bonded oxygen is NOx.

8. A method of measuring a predetermined measurement gas component in a measurement gas, comprising the steps of:

introducing said measurement gas containing said measuremet gas component having bonded oxygen to be measured, from an external measurement gas space into a first processing zone under a predetermined diffusion resistance;

pumping out oxygen in said first processing zone by the aid of an oxygen-pumping action effected by a first electrochemical pumping cell so that a partial pressure of oxygen in an atmosphere in said first processing zone is lowered to a degree sufficient to control a partial pressure of oxygen in a subsequent second processing zone;

introducing said atmosphere into said second processing zone under a predetermined diffusion resistance, said second processing zone being in serial communication with said first processing zone;

pumping out oxygen in an atmosphere in said second processing zone by the aid of a second electrochemical pumping cell so that said partial pressure of oxygen in said atmosphere is controlled to have a low value of partial pressure of oxygen which does not substantially affect measurement of an amount of said measurement gas component;

introducing said atmosphere into a third processing zone under a predetermined diffusion resistance, said third processing zone being in serial communication with said second processing zone;

reducing or decomposing said measurement gas component introduced from said second processing zone, in an atmosphere in said third processing zone; and outputting, with the use of an electrochemical sensor cell, an electromotive force corresponding to a partial pressure of oxygen in said atmosphere in said third processing zone, defined by oxygen produced in said reducing or decomposing step to obtain a detected output value from which said amount of said measurement gas component in said measurement gas is determined.

9. The method according to claim 8, wherein said first and second electrochemical pumping cells and said electrochemical sensor cell are heated to a predetermined temperature respectively.

10. The method according to claim 8, wherein said partial pressure of oxygen in said atmosphere in said first processing zone is controlled by detecting said partial pressure of oxygen in said measurement gas in said first processing zone, changing a voltage of a power source on the basis of an obtained detected value, and controlling said oxygen-pumping action effected by said first electrochemical pumping cell.

11. The method according to claim 8, wherein said second and third processing zones are provided in one internal space.

12. The method according to claim 8, wherein a pumping voltage applied to said second electrochemical pumping cell is substantially the same as an electromotive force based on said partial pressure of oxygen in said atmosphere in said first processing zone.

13. The method according to claim 8, wherein said measurement gas component having bonded oxygen is NOx.

14. A sensing device for measuring an amount of a predetermined measurement gas component in a measurement gas by measuring an amount of oxygen produced by reducing or decomposing said measurement gas component having bonded oxygen in said measurement gas, said sensing device comprising:

a first processing zone comparted from the outside, said first processing zone communicating with an external measurement gas space;

a first diffusion rate-determining means for introducing said measurement gas containing said measurement gas component, from said measurement gas space into said first processing zone under a predetermined diffusion resistance;

a first electrochemical pumping cell comprising a first oxygen ion-conductive solid electrolyte and a pair of electrodes provided in contact therewith, for pumping out oxygen from said first processing zone by applying a current between said pair of electrodes so that a partial pressure of oxygen in an atmosphere in said first processing zone is lowered to a degree sufficient to control a partial pressure of oxygen in a subsequent second processing zone;

said second processing zone comparted from the outside, said second processing zone communicating serially with said first processing zone;

a second diffusion rate-determining means for introducing said atmosphere in said first processing zone having said lowered partial pressure of oxygen into said second processing zone under a predetermined diffusion resistance;

a second electrochemical pumping cell comprising a second oxygen ion-conductive solid electrolyte and a pair of electrodes provided in contact therewith, for pumping out oxygen from said second processing zone by applying a current between said pair of electrodes so that a partial pressure of oxygen in an atmosphere in said second processing zone is controlled to have a low value of partial pressure of oxygen which does not substantially affect measurement of said amount of said measurement gas component;

a third processing zone comparted from the outside, said third processing zone communicating serially with said second processing zone, for reducing or decomposing said measurement gas component in an atmosphere introduced from said second processing zone;

a third diffusion rate-determining means for introducing said atmosphere in said second processing zone having said controlled partial pressure of oxygen into said third processing zone under a predetermined diffusion resistance;

a third electrochemical pumping cell comprising a third oxygen ion-conductive solid electrolyte and a pair of electrodes provided in contact therewith, for pumping out oxygen produced by reducing or decomposing said measurement gas component in said third processing zone, by applying a current between said pair of electrodes; and a current-detecting means for detecting said pumping current allowed to flow by the aid of an pumping action effected by said third electrochemical pumping cell.

15. The sensing device according to claim 14, further comprising a heating means capable of heating said first, second, and third electrochemical pumping cells to a predetermined temperature respectively.

16. The sensing device according to claim 14, wherein a catalyst for reducing or decomposing said measurement gas component to produce oxygen is arranged in said third processing zone.

17. The sensing device according to claim 14, wherein said third oxygen ion-conductive solid electrolyte of said third electrochemical pumping cell constitutes at least a part of a partition wall for comparting said third processing zone, one of said pair of electrodes provided in contact therewith is arranged at a position in said third processing zone, and said electrode arranged in said third processing zone also functions as a catalyst for reducing or decomposing said measurement gas component to produce oxygen.

18. The sensing device according to claim 17, wherein said electrode arranged in said third processing zone is composed of a porous cermet comprising a ceramic and a metal capable of reducing or decomposing said measurement gas component having bonded oxygen.

19. The sensing device according to claim 14, further comprising a partial oxygen pressure-detecting means for detecting said partial pressure of oxygen in said first processing zone, wherein said partial pressure of oxygen in said first processing zone is controlled by controlling a voltage applied to said first electrochemical pumping cell, on the basis of a value of partial pressure of oxygen detected by said partial oxygen pressure-detecting means.

20. The sensing device according to claim 14, wherein said second and third processing zones are constructed by one thinly gapped flat space having a predetermined diffusion resistance so that an inlet section of said flat space is used as said second processing zone, and an inner section of said flat space is used as said third processing zone.

21. The sensing device according to claim 14, wherein said second diffusion rate-determining means is principally composed of a porous material having a predetermined diffusion resistance, arranged and packed in a communicating passage between said first and second processing zones.

22. The sensing device according to claim 14, wherein said third diffusion rate-determining means is principally composed of a porous material having a predetermined diffusion resistance, arranged and packed in a communicating passage between said second and third processing zones.

23. A sensing device for measuring an amount of a predetermined measurement gas component in a measurement gas by measuring an amount of oxygen produced by reducing or decomposing said measurement gas component having bonded oxygen in said measurement gas, said sensing device comprising:

a first processing zone comparted from the outside, said first processing zone communicating with an external measurement gas space;

a first diffusion rate-determining means for introducing said measurement gas containing said measurement gas component, from said measurement gas space into said first processing zone under a predetermined diffusion resistance;

a first electrochemical pumping cell comprising a first oxygen ion-conductive solid electrolyte and a pair of electrodes provided in contact therewith, for pumping out oxygen from said first processing zone by applying a current between said pair of electrodes so that a partial pressure of oxygen in an atmosphere in said first processing zone is lowered to a degree sufficient to control a partial pressure of oxygen in a subsequent second processing zone;

said second processing zone comparted from the outside, said second processing zone communicating serially with said first processing zone;

a second diffusion rate-determining means for introducing said atmosphere in said first processing zone having said lowered partial pressure of oxygen into said second processing zone under a predetermined diffusion resistance;

a second electrochemical pumping cell comprising a second oxygen ion-conductive solid electrolyte and a pair of electrodes provided in contact therewith, for pumping out oxygen from said second processing zone by applying a current between said pair of electrodes so that a partial pressure of oxygen in an atmosphere in said second processing zone is controlled to have a low value of partial pressure of oxygen which does not substantially affect measurement of said amount of said measurement gas component;

a third processing zone comparted from the outside, said third processing zone communicating serially with said second processing zone, for reducing or decomposing said measurement gas component in an atmosphere introduced from said second processing zone;

a third diffusion rate-determining means for introducing said atmosphere in said second processing zone having said controlled partial pressure of oxygen into said third processing zone under a predetermined diffusion resistance;

an electrochemical sensor cell comprising a fourth oxygen ion-conductive solid electrolyte and a pair of electrodes provided in contact therewith, for outputting an electromotive force corresponding to a partial pressure of oxygen in said atmosphere in said third processing zone, defined by oxygen produced by reducing or decomposing said measurement gas component; and a voltage-detecting means for detecting said electromotive force outputted from said electrochemical sensor cell.

24. The sensing device according to claim 23, further comprising a heating means capable of heating said first and second electrochemical pumping cells and said electrochemical sensor cell to a predetermined temperature respectively.

25. The sensing device according to claim 23, wherein a catalyst for reducing or decomposing said measurement gas component to produce oxygen is arranged in said third processing zone.

26. The sensing device according to claim 23, wherein said fourth oxygen ion-conductive solid electrolyte of said electrochemical sensor cell constitutes at least a part of a partition wall for comparting said third processing zone, one of said pair of electrodes provided in contact therewith is arranged at a position in said third processing zone, and said electrode arranged in said third processing zone also functions as a catalyst for reducing or decomposing said measurement gas component to produce oxygen.

27. The sensing device according to claim 26, wherein said electrode arranged in said third processing zone is composed of a porous cermet comprising a ceramic and a metal capable of reducing or decomposing said measurement gas component having bonded oxygen.

28. The sensing device according to claim 23, further comprising a partial oxygen pressure-detecting means for detecting said partial pressure of oxygen in said first processing zone, wherein said partial pressure of oxygen in said first processing zone is controlled by controlling a voltage applied to said first electrochemical pumping cell, on the basis of a value of partial pressure of oxygen detected by said partial oxygen pressure-detecting means.

29. The sensing device according to claim 23, wherein said second and third processing zones are constructed by one thinly gapped flat space having a predetermined diffusion resistance so that an inlet section of said flat space is used as said second processing zone, and an inner section of said flat space is used as said third processing zone.

30. The sensing device according to claim 23, wherein said second diffusion rate-determining means is principally composed of a porous material having a predetermined diffusion resistance, arranged and packed in a communicating passage between said first and second processing zones.

31. The sensing device according to claim 23, wherein said third diffusion rate-determining means is principally composed of a porous material having a predetermined diffusion resistance, arranged and packed in a communicating passage between said second and third processing zones.

* * * * *